(12) United States Patent
Keckstein et al.

(10) Patent No.: US 6,221,008 B1
(45) Date of Patent: Apr. 24, 2001

(54) DEVICE FOR LIFTING THE ABDOMINAL WALL FOR LAPAROSCOPY

(75) Inventors: Jörg Keckstein, Villach; Uwe Bacher, Tuttlingen; Markus Lehmann, Wurmlingen, all of (DE)

(73) Assignee: Karl Storz GmbH & Co., KG (DE)

( * ) Notice: Subject to any disclaimer, the term of this patent is extended or adjusted under 35 U.S.C. 154(b) by 0 days.

(21) Appl. No.: 09/117,945

(22) PCT Filed: Feb. 10, 1997

(86) PCT No.: PCT/DE97/00254

§ 371 Date: Mar. 29, 1999

§ 102(e) Date: Mar. 29, 1999

(87) PCT Pub. No.: WO97/28747

PCT Pub. Date: Aug. 14, 1997

(30) Foreign Application Priority Data

Feb. 8, 1996 (DE) .............................................. 196 04 618

(51) Int. Cl.⁷ ...................................................... A61B 1/32
(52) U.S. Cl. ............................................. 600/204; 600/214
(58) Field of Search .................................. 600/201, 204, 600/210, 214, 219, 235

(56) References Cited

U.S. PATENT DOCUMENTS 5,195,505 * 3/1993 Josefsen ................................ 600/204
5,289,817 * 3/1994 Williams et al. ..................... 600/204
5,381,788 * 1/1995 Matula et al. ........................ 600/214
5,702,352 * 12/1997 Kimura et al. ....................... 600/201
5,722,935 * 3/1998 Christian ......................... 600/204 X

FOREIGN PATENT DOCUMENTS 640 126    12/1936   (DE) .
9106553    9/1991    (DE) .
0 614 646  9/1994    (EP) .
1532001  * 12/1989   (SU) ................................... 600/214

* cited by examiner

Primary Examiner—Jeffrey A. Smith
(74) Attorney, Agent, or Firm—St.Onge Steward Johnston & Reens LLC

(57) ABSTRACT

Disclosed is a device for lifting the abdominal wall for laparoscopy, whereby the device can be inserted into the abdominal cavity through an opening in the abdominal wall, having an instrument shaft, which is provided at its distal end region with at least one, preferably two limbs disposed parallel to the axis of the instrument shaft and the can be folded open laterally to the shaft axis. The invention is distinguished by the limbs being joined to the instrument shaft via a folding mechanism, which rotates the limbs at an angle ranging up to 180°.

20 Claims, 3 Drawing Sheets

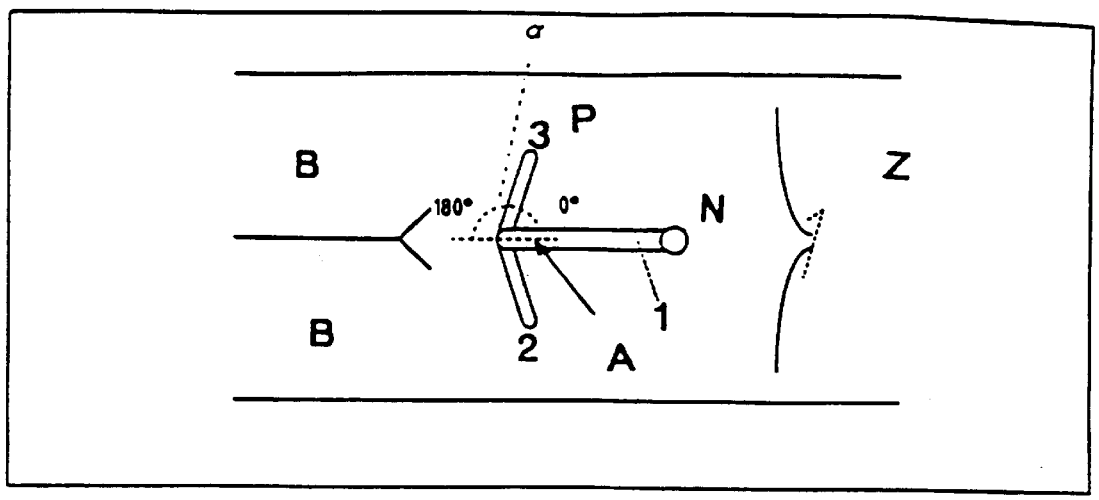
Fig. 1
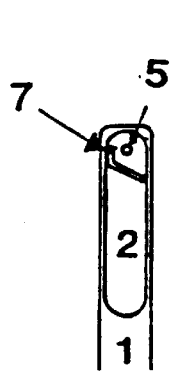 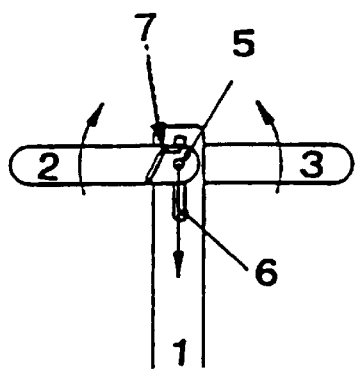 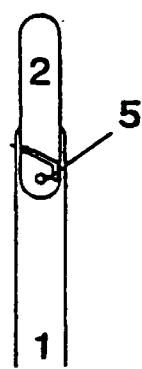
Fig. 2a  Fig. 2b  Fig. 2c

DEVICE FOR LIFTING THE ABDOMINAL WALL FOR LAPAROSCOPY

TECHNICAL FIELD

The present invention relates to a device for lifting the abdominal wall for laparoscopy, whereby this device can be at least partially inserted into the abdomen through an opening in the abdominal wall.

STATE OF THE ART

Generic type devices possess an instrument shaft which is provided at its distal end region with at least one, preferably two parallel limbs disposed parallel to the axis of the instrument shaft. The limbs can be folded open laterally to the axis of the shaft.

Devices of the above class, employed in the field of endoscopic surgery, for laparoscopy respectively laparoscopic treatment, are also known under the term "elevation instruments" Instruments of this type are inserted into the abdominal cavity through a narrow opening and, by folding the holding supports open laterally, provide a wide fan support in order to be able to lift as large as possible an area of the abdominal wall. In this way, the surgical area required inside the abdominal lumen is created for subsequent laparoscopy as well as endoscope-supported surgery.

The elevation instruments used for widening the abdominal cavity, should, on the one hand, have a small as possible cross section so that the opening in the abdominal wall through which the instrument is inserted inside the abdomen can be maintained as small as possible and, on the other hand, however the carrier arms or hereinafter called limbs, which can be folded open laterally to the side of the instrument offer a wide as possible fan support for the abdominal wall.

The following demands are made on the rotating respectively folding mechanism, by which the limbs are folded away from the axis of the instrument:

The folding open and shut procedure should occur inside the abdominal cavity in a reliable and dosed manner. The whole carrier mechanism should be provided with sufficient stability for bearing the weight of the abdominal wall and at the same time require as little space as possible. Furthermore, safety devices should be provided in order to be able to remove the elevation instrument from the abdomen again if the folding mechanism fails.

The article by Albert K. Chin et al., "Gasless Laparoscopy Using a Planar Lifting Technique", in the Journal of the American College of Surgeons, April 19194, vol. 178, pp. 401–403, describes a generic type device for mechanically lifting the abdominal wall which permits carrying out laparoscopic surgery without continuous gas insufflation into the abdominal cavity. The gas bubble inside the abdominal cavity created by the insufflation of, preferably, carbon dioxide can lead to reducing the breathing capacity and diminished vein return flow due to the artificial maintenance of a relatively high pressure. Generic type elevation instruments are utilized in order to avoid this and other drawbacks for the patient.

The generic type device described in the aforementioned article provides for a handling shaft at the distal end region of which an expanding device, which assumes a closed position for insertion into the abdominal cavity, is attached at a right angle to the axis of the shaft so that the expanding shaft can be brought into the abdominal cavity through very narrow abdominal openings. Due to an operating mechanism attached to the handling shaft, the folding mechanism can be folded open scissorlike inside the abdominal cavity, whereby two limbs provided in a V position lift the abdominal wall intracorporally by appropriate lifting of the instrument.

Removal of the device is not possible until the limbs set in the V position have been returned to a parallel position by the corresponding operating mechanism. However, if pieces of tissue are present between the limbs, these may be bruised or irreversibly damaged when the limbs are closed again. Moreover, in such an event, complete closing of the two limbs is impossible, thereby considerably impeding gentle removal of the instrument through the small opening in the abdomen.

Furthermore, generic type devices are known which provide limbs that can be folded open parallel to the axis of the shaft of the instrument, which following insertion into the abdominal cavity through very narrow abdominal openings fold open inside the abdominal cavity like the mechanism of an umbrella and with appropriate lifting of the instrument lift the abdominal wall intracorporally from below in the direction of the movement of the instrument. With these type of folding mechanisms, which preferably occupy a region of rotation between the parallel position to the axis of the shaft and an orthogonal position to the axis of the shaft, the problem arises that pieces of tissue in the abdominal cavity can considerably impede closing the limbs again. However, incomplete closing of the individual limbs leads to a kind of catching, the removal of which through the small abdominal opening inevitably damages the tissue surrounding the abdominal opening.

DESCRIPTION OF THE INVENTION

The object of the present invention is to improve a device for lifting the abdominal wall for laparoscopy according to the generic part of claim 1 in such a manner that the aforedescribed risk of incomplete closing of the instrument limbs expanded for lifting the abdominal wall due to, for example catching or pinching pieces of tissue, is largely ruled out. For this purpose, a folding mechanism should be used for folding the expanding limbs open with as little use of space as possible in order to avoid intracorporal tissue irritation. Nonetheless, the instrument should be easy to operate without requiring major force.

A solution to the object is set forth. Further features which advantageously improve the concept of the solution are disclosed.

An element of the present invention is to improve a device for lifting the abdominal wall for laparoscopy in such a manner that the limbs are joined with the shaft of the instrument via a folding mechanism which rotates the limbs at an angle range up to 180°.

In this manner, for removal of the instrument out of the abdominal cavity, the limbs folded open for lifting, preferably in an orthogonal position to the shaft of the instrument, can be folded either to the proximal side of the instrument parallel to the axis of the shaft of the instrument or, if the limbs are prevented from fitting completely close to the axis of the instrument by caught pieces of tissue, to fold in the opposite direction, i.e. toward the distal side, until the limbs fit closely parallel to the axis of the shaft of the instrument in order to be able to remove the instrument in this position easily from the abdominal cavity through the abdominal opening.

BRIEF DESCRIPTION OF THE DRAWING

The invented 180° folding mechanism is made more apparent by way of example using a preferred embodiment with reference to the accompanying drawings, showing in:

FIG. 1 a basic sketch of an invented elevation instrument for use in a patient's abdominal cavity, FIG. 2A is a diagrammatic view of an invented folding mechanism during insertion, FIG. 2B is a diagrammatic view of an invented folding machine with partially unfolded limbs, FIG. 2C is a view similar to a view if FIG. 2B but illustrating fully unfolded limbs, FIG. 3 a diagram of the distal end region of the shaft of the instrument, FIG. 4 a top view of a shaft having an integrated guide track, and FIG. 5 a representation of the force conditions in the control curve.

DESCRIPTION OF A PREFERRED EMBODIMENT

Figure 3:
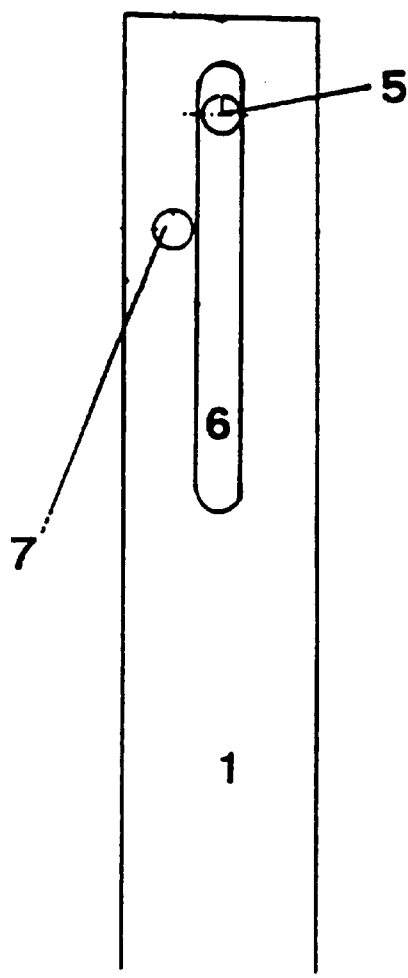

FIG. 1 is a diagrammatic top view of a patient P, whose legs B and diaphragm Z are shown. The elevation instrument is inserted inside the body through a corporal opening N. The elevation instrument is provided with an instrument shaft 1 and two limbs 2 and 3 which can be folded open laterally to the axis A of instrument shaft 1. An element of the present invention is that the limbs 2 and 3 can be rotated at an angle range of $0° \leq \alpha \leq 180°$.

The positions $\alpha=0°$ correspond to the limb position for insertion of the instrument through the abdominal opening N. If the limbs can no longer be folded back to the initial position, be it due to caught pieces of tissue or mechanical failure, both limbs can be folded to the 180° position. In this manner, the ability to remove the instrument again through the abdominal opening N is given in any event.

The details of FIGS. 2a to 2c show the basic principle of the folding mechanism. In side views of the distal end region of the invented device, on instrument shaft 1 in the representation according to FIG. 2a, a limb 2 is shown in parallel position to the axis of the shaft. In this arrangement, the instrument shaft is brought inside the abdomen through a abdominal opening, not depicted in the figure. Fundamentally, the foldable limbs 2 and 3 each are provided with a control curve 4 (FIG. 4) which is integrated in a lateral end region of each limb. Control curve 4 may be designed as a groove or as a slit running completely through the material of the limb.

In addition to control curve 4, each limb is provided with a rotatable, moveable joining means 5. Joining means 5 projects through a guide track 6 designed as a slit, which is integrated in the distal region of instrument shaft 1 and joins in this manner the two limbs 2 and 3. In addition to guide track 6, the distal region of instrument shaft 1 is provided per limb side with a control pin 7 which is fixedly attached to the instrument shaft and which projects through the control curve 4 of the respective limb.

With the aid of the resulting folding mechanism, the limbs can be brought from the parallel position according to FIG. 2a into the orthogonal position according to FIG. 2b by moving the joining means proximally along the guide track 6.

Due to the axial movement of joining means 5 along guide track 6, each limb experiences a torque as a result of control pin 7 engaging in the control curve, which torque rotates the limbs about the joining means 51 which is simultaneously also the rotating center of the limbs, and therewith each limb also experiences a tilting indicated by the curved arrows. If joining means 5 is located at the end of guide track 6 facing the proximal side, both limbs are aligned parallel to the axis of the instrument at the distal side (for this see FIG. 2c).

The kinematic triggering of joining means 5 for axial movement occurs via an operating element, not depicted in FIG. 2, which may be executed in the form of a connecting rod. Depending on the position of the limbs, they can be stopped in their position by means of the connecting rod.

FIG. 3 shows a diagrammatic view of an advantageous embodiment of the distal end region of an instrument shaft 1. The control pin, which engages in the control curve of the respective limb, is fixedly disposed laterally beside guide track 6. The longitudinally moveable joining means 5, which projects through guide track 6 of the instrument shaft and joins kinematically both limbs, can be stopped in each position by means of a not depicted operating element.

Figure 4:
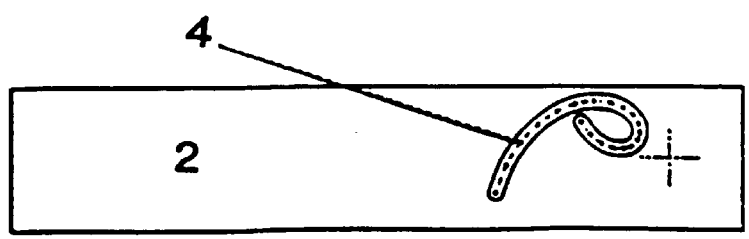

FIG. 4 shows an advantageously designed limb 2 which is provided with a cross which indicates the point of penetration of joining means 5. The particularly advantageously designed control curve is designed in such a manner that it is integrated completely in the limb region and does not intersect itself.

The control curve form shown in FIG. 4 permits, in particular, that uniform moving of the joining means leads to a uniform movement of the limbs about their point of rotation.

Figure 5:
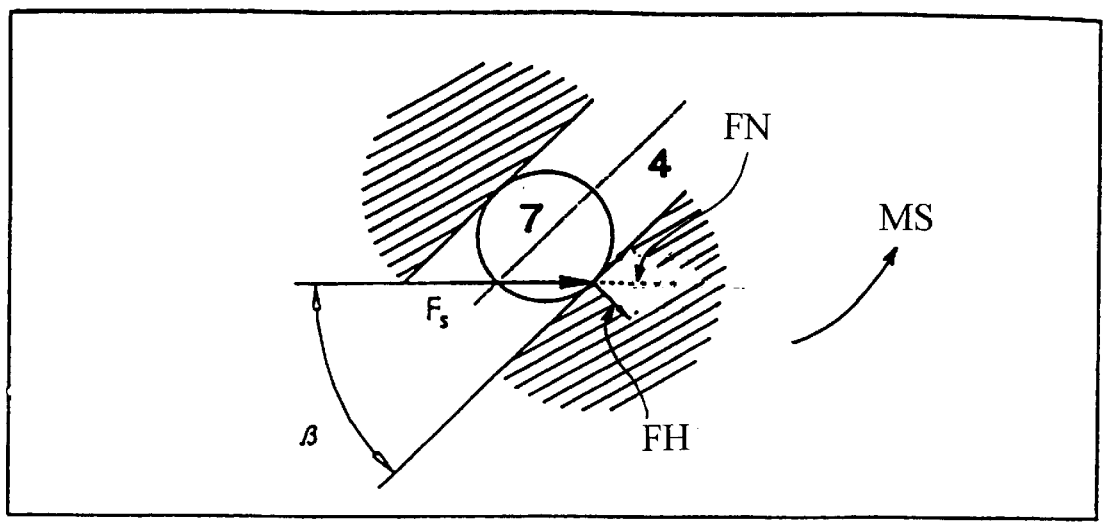

The folding movement of the limbs is generated by a torque which occurs by guiding the control pin inside the control curve. By means of the sliding movement of the control pin inside the control curve, the latter exercises a force FS on the external contour of the curved groove. This is shown in FIG. 5. Force conditions of a self-acting incline set in. Thus force FS divides into the components descending incline force FH and normal force FN. Normal force FN is responsible for the movement of the limbs. The larger their share in the force plan is, the more force is at disposal for generating the moment MS. However, with increasing normal force, the surface pressure between the pin and the contour of the control curve also increases and therefore also the work consumed by friction required for the movement.

In order for the control pin to be able to run easily through the curve contour, the share of the component descending incline force FH is selected not too small. The angle β should therefore not be larger than 65° at any point of the curve. In this manner it is ensured that at least ¼ of the required force occurs as descending incline force.

What is claimed is:

1. A device for lifting the abdominal wall for laparoscopy, whereby said device can be inserted into the abdominal cavity through an opening in the abdominal wall, said device having an instrument shaft, which is provided at its distal end region with at least one limb disposed parallel to an axis of said instrument shaft, said at least one limb can be folded open laterally to said shaft axis, said device characterized by the fact that said at least one limb are joined to said instrument shaft via a folding mechanism, which rotates said at least one limb at an angle ranging up to 180°.

2. A device according to claim 1, characterized by the fact that said at least one limb has a flattened rod shape and a width corresponding maximally to that of a distal width of said instrument shaft.

3. A device according to claim 1, characterized by the fact that an operating element is provided which actuates said folding mechanism from the proximal side of said instrument shaft.

4. A device according to claim 1, characterized by the fact that said at least one limb can be stopped at least in one position perpendicular to said axis of said instrument shaft.

5. A device according to claim 1, characterized by the fact that two limbs disposed on an instrument shaft are fixedly joined to each other in a rotatable manner via a pin-like joining means which at the same time forms a common axis of rotation of said limbs.

6. A device for lifting the abdominal wall for laparoscopy, whereby said device can be inserted into the abdominal cavity through an opening in the abdominal wall, said device having an instrument shaft, which is provided at its distal end region with at least one limb disposed parallel to an axis of said instrument shaft, said at least one limb can be folded open laterally to said shaft axis, said device characterized by the fact that said instrument shaft is provided in its distal end region with a guide track running parallel to said axis, said at least one limb is joined to said instrument shaft via a folding mechanism, which rotates said limbs at an angle up to 180.

7. A device according to claim 6, characterized by the fact that said guide track is a groove or a guide slit running completely through said instrument shaft.

8. A device according to claim 6, characterized by the fact that said at least one limb is provided in one of its lateral end regions with a control curve and a pin-like joining means which fixedly joins said at least one limb in a rotatable manner about said joining means and in a moveable manner along said guide track of said instrument shaft.

9. A device according to one of the claim 8, characterized by the fact that said control curve is designed as a slit.

10. A device according to claim 8, characterized by the fact that by means of moving said joining means along said guide track of said instrument shaft, said folding mechanism effects a lateral excursion of said at least one limbs by means of the resulting relative movement of said control pin inside said control curve.

11. A device according to claim 10, characterized by the fact that an operating element is provided which actuates said folding mechanism from the proximal side of said instrument shaft.

12. A device according to claim 11, characterized by the fact that said operating element engages actively with said joining means.

13. A device according to claim 8 characterized by the fact that an operating element engages actively with said joining means.

14. A device for lifting the abdominal wall for laparscopy, whereby said device can be inserted into the abdominal cavity through an opening in the abdominal wall, said device having an instrument shaft, which is provided at its distal end region with at least one limb disposed parallel to an axis of said instrument shaft, said at least one limb can be folded open laterally to said shaft axis, said device characterized by the fact that said at least one limb is joined to said instrument shaft via a folding mechanism including a guide track running parallel to said axis of the instrument shaft, which rotates said at least one limb at an angle.

15. A device according to claim 14, characterized by the fact that said at least one limb is provided in one of its lateral end regions with a control curve and a pin-like joining means which fixedly joins said at least one limb in a rotatable manner about said joining means and in a moveable manner along said guide track of said instrument shaft.

16. A device according to claim 15, characterized by the fact that said control curve engages with a control pin fixedly attached on said instrument shaft.

17. A device for lifting the abdominal wall for laparoscopy, whereby said device can be inserted into the abdominal cavity through an opening in the abdominal wall, said device having an instrument shaft, which is provided at its distal end region with at least one limb disposed parallel to an axis of said instrument shaft, said at least one limb can be folded open laterally to said shaft axis, said device characterized by the fact that said at least one limb is joined to said instrument shaft via a folding mechanism, said at least one limb is provided in one of its lateral end regions with a control curve and a pin-like joining means which fixedly joins at least one limb in a rotatable manner about said joining means and in a movable manner along a guide track of said instrument shaft.

18. A device according to claim 17, characterized by the fact that said control curve engages with a control pin fixedly attached on said instrument shaft.

19. A device according to claim 18, characterized by the fact that two limbs disposed on an instrument shaft are fixedly joined to each other in a rotatable manner via a pin-like joining means which at the same time forms a common axis of rotation of said limbs.

20. A device for lifting the abdominal wall for laparoscopy, comprising:

an elongated shaft extending along a longitudinal axis and having a distal end;

a pair of limbs mounted on the distal end of the elongated shaft;

a folding mechanism on said elongated shaft and connected to the pair of limbs to rotate them in opposite directions at a 180 angle between first and second positions, wherein the limbs extend parallel to the longitudinal axis.

* * * * *